United States Patent [19]
Lyza, Jr.

[11] Patent Number: 5,976,112
[45] Date of Patent: Nov. 2, 1999

[54] INJECTOR SYRINGE

[75] Inventor: Henry Walter Lyza, Jr., Lynwood, Ill.

[73] Assignee: LyZa Weiss Jennings & Shea, Lynwood, Ill.

[21] Appl. No.: 08/966,056

[22] Filed: Nov. 7, 1997

[51] Int. Cl.$^6$ ..................................................... A61M 5/32
[52] U.S. Cl. ........................... 604/199; 427/2.3; 604/226
[58] Field of Search .................................. 264/524, 525; 427/2.3; 128/844; 604/199, 111, 118, 119, 208, 218, 220, 221, 226

[56] References Cited

U.S. PATENT DOCUMENTS

| | | |
|---|---|---|
| 3,661,152 | 5/1972 | Beich et al. ........................ 604/218 X |
| 3,738,539 | 6/1973 | Beich ................................. 604/218 X |
| 3,878,846 | 4/1975 | Rimbaud . |
| 3,930,499 | 1/1976 | Rimbaud . |
| 4,210,173 | 7/1980 | Choksi et al. . |
| 4,444,062 | 4/1984 | Bennett et al. . |
| 4,511,534 | 4/1985 | Bennett, Jr. et al. . |
| 4,673,386 | 6/1987 | Gordon . |
| 4,677,980 | 7/1987 | Reilly et al. . |
| 4,940,527 | 7/1990 | Kazlauskas et al. . |
| 5,130,159 | 7/1992 | Shienker et al. . |
| 5,135,489 | 8/1992 | Jepson et al. . |
| 5,158,554 | 10/1992 | Jepson et al. . |
| 5,167,648 | 12/1992 | Jepson et al. . |
| 5,171,234 | 12/1992 | Jepson et al. . |
| 5,324,266 | 6/1994 | Ambrisco et al. . |
| 5,354,272 | 10/1994 | Swendson et al. . |
| 5,474,546 | 12/1995 | Ambrisco et al. . |
| 5,536,471 | 7/1996 | Clark et al. . |

OTHER PUBLICATIONS two (2) company brochures by Medrad, Inc. entitled "The most trusted injector" and "In the selection of syringers, some choices are clear".

PCT Search Report, Mailed Jan. 13, 1999.
Abbott In–Line Sampling System (Photographs), Date Unknown.
Baxter Product Literature for CO–Set and Closed Injectate Delivery System for Room Temperature Injectate Model 93–610, Oct. 1995.
Baxter Product Literature for Venous/Arterial Blood Management Protection System, Oct. 1994.
Abbott Laboratories Product Literature for Thermoset–Iced for Use with In–Line Thermister Probe and Colling Container, Jan. 1998.
Abbott Laboratories Product Literature for Thermoset–Closed Coop Injectable Delivery System for Cold Injectate, Circa 1990.

*Primary Examiner*—Wynn Wood Coggins
*Assistant Examiner*—A. T. Nguyen
*Attorney, Agent, or Firm*—Juettner Pyle Piontek & Underwood

[57] ABSTRACT

An injection syringe for injecting a fluid into the arterial, venous, muscular or cavity structures of a patient via subcutaneous, percutaneous, intravascular and other types of injections comprises a hollow syringe body, a passageway at a distal end of the syringe for passage of fluid into and out of the syringe and a substantially open proximal end for receiving a plunger assembly. The plunger assembly includes a movable plunger assembly. A moveable plunger cooperates with the syringe body and the proximal end of the syringe to define a fluid chamber of variable volume in fluid communication with the passageway. Actuating means actuates movement of the plunger. An elastomeric barrier cooperates with the plunger and the open end of the syringe to define a sterile chamber between the actuating means and the fluid chamber to prevent passage of fluids from the fluid chamber to the actuating means and the passage of contaminants from the open end of the syringe in the fluid chamber.

50 Claims, 7 Drawing Sheets

INJECTOR SYRINGE

FIELD OF THE INVENTION

The present disclosure relates to an improved injection syringe. More particularly, this disclosure teaches an injector syringe for septically injecting a contrast medium into a patient without contamination or substantial risk of an embolism, where a resilient membrane is juxtaposed between a sterile fluid chamber and a non-sterile plunger actuating means, the membrane acting as a physical and sanitary barrier against contaminants and air entering the sterile portions of the syringe.

BACKGROUND

Syringes for injecting various fluids into the arterial, venous, muscular and cavity structures of a patient via subcutaneous, percutaneous, intravascular and other types of injections are widely known and used. As herein use, the term "patient" generally refers to any individual subject to medical treatment, study or examination, including humans and so-called lower animals. Generally stated, a molded tubular body or barrel defines these syringes having a plunger at one end and a needle or other device for subcutaneous, percutaneous or other intravascular injection-type access at an opposite end. Retraction of the plunger fills the fluid chamber within the syringe with a desired fluid of the plunger, creating a vacuum and drawing fluid therein. Once filled to the desired volume of fluid, the plunger can be advanced within the barrel to force the fluid through the needle or other device subcutaneously, percutaneously or otherwise disposed appropriately to introduce the fluid within the patient.

Such syringes have been enormously useful in promoting and maintaining the health of humankind and in treating a variety of ailments, especially as hand-held and manually manipulated syringes. Such devices have also been adapted for diagnostic purposes, such as, for example, in angiographic applications. There, contrast media is injected into a patient for diagnosis of any number of different conditions. Such latter applications are more commonly performed today using machine-driven and/or automated devices controllably to inject the contrast media. Also, in such latter applications, reusing the syringe for multiple injections of contrast media into the same patient is desirable for many reasons, for example, to reduce costs, avoid entrained air that can lead to embolisms and minimize the examination time to avoid pericatheter thrombus.

However, these devices have the disadvantage that after they advance the plunger while the needle or other device remains subcutaneously, percutaneously or otherwise disposed, any retraction of the plunger draws bodily fluids back into the syringe. While this has always been a problem, the consequence of the HIV virus and acquired autoimmunity deficiency syndrome (AIDS) has made such backfilling fraught with dire results if the contaminants withdrawn are not otherwise contained.

Also, particularly in machine-driven and/or automated devices, dust, oils and latent biological matter from previous use are usually present near the interface between the drive mechanism and the syringe and surrounding structures, such as pressure jackets that hold the syringe. Thus, an additional disadvantage of the syringes of the prior art was that such contaminants can enter the syringe body and adhere to the inner walls of the syringe, with the possible introduction of such contaminants into the fluid chamber and, ultimately, the patient. This could result in cross-contamination of certain diseases from patient to patient such as Hepatitis B, Hepatitis C, AIDS and other blood-borne pathogens.

Because of these drawbacks, especially bodily fluids from previous patients becoming entrained into the syringe upon withdrawal of the plunger in diagnostic uses, it is typically not recommended that the syringe be used for more than one injection of contrast material. Although this reduces contamination of the mechanisms used to drive the plunger and contaminants entering the syringe from the drive mechanism or other sources from the open end of the syringe, the safety of the patient is compromised. Each time a new syringe is used, an opportunity exists for air to enter the fluid in communication with the patient, thus leading to the potential for an embolism. Also, in especially angiographic or vascular studies, prolonging the examination can result in pericatheter thrombus.

An approach to partially addressing these drawbacks, at least regarding automated or mechanical applications, is shown in U.S. Pat. No. 4,677,980. This reference shows an angiographic injector system having two angiographic injectors situated on a turret. Each injector is provided with a releasable connector for connecting the plunger to a driving mechanism for an injection operation and disconnecting the plunger from the driving mechanism after the injection operation so as not to draw body fluids of a patient back into the syringe.

While effective when used properly, the device taught by U.S. Pat. No. 4,677,980 does not guarantee the containment of pathogens borne in bodily fluids within the syringe. Much discretion remains with the operator of the injector mechanism and is still possible that withdrawal of the plunger can occur while the injector syringe remains in fluid communication with the venous, arterial or muscular system or cavity structures of the patient, thereby allowing bodily fluids to enter the syringe. Although the syringe is usually discarded after a single use on a single patient, the risk remains that the withdrawn bodily fluids may pass past the sides of the plunger to the exposed, non-sterile base of the plunger connected to the driving mechanism. The resulting contamination of the driving mechanism creates significant problems in cleaning, such as wasted time and lost machine productivity. Also, there is no effective method of ensuring that contaminants do not enter the syringe from the drive mechanism or otherwise.

Perhaps more important, the use of a new syringe for each contrast media injection requires repeated operations of disconnecting fluid communication with the patient from the old syringe, adding fluid to the new syringe and reestablishing fluid communication with the new syringe to the patient, each operation introducing the risk of embolisms and pericatheter thrombus.

Other approaches to avoid contamination exist, although none solve the aforementioned problems. One example is U.S. Pat. No. 4,511,534, which shows a liquid transfer device comprising a one-piece molded pipette plate having some pipette-type barrels extending downwardly. An annular upstanding boss surrounds the upper end of each barrel and support flange extending about the perimeter of the pipette plate. An elastic membrane extends over and rests on each annular boss. A membrane retaining plate, having through passages disposed in alignment with a barrel or pipette on the pipette plate and having a downwardly protruding boss, surrounds each aperture and extends in the respective upstanding boss on the pipette plate. Connecting means maintains the retaining plate in a first position compared with the pipette plate, where the bosses engage the elastic membrane with minimal tension, and a second position, where the bosses on the retaining plate and the pipette plate clamp the elastic membrane under tension with part of the elastic membrane extending into each of the pipettes' barrels.

However, in U.S. Pat. No. 4,511,534, the membrane is not shown as applicable to a syringe application. More important, its membrane is in direct contact with the fluid, providing no intermediate volume isolating the fluid chamber from the open end of the assembly. With such an arrangement, surface treatments, such as powder often present on elastomeric membranes, would be in contact with the fluid to be injected into the patient. Also, extraneous outside contaminants are not fully isolated.

The known prior art is thus lacking a syringe with means designed to isolate a sterile inner chamber of a syringe from contamination that might otherwise enter the syringe from various sources, such as from the drive mechanism into the open rear end of the syringe. The barrier means or membrane of the present disclosure prevents such further contamination. Also, since the barrier means of the present disclosure does not come into direct contact with the contrast medium or the like, reactions of patients that may be sensitive to the barrier means, for example, a latex membrane, is eliminated.

Also, an important advantage of the present disclosure is that the syringe herein revealed can be used multiple times on a single patient. Since the possibility of cross-contamination and air emboli injection is most acute during the setup procedures used with the installation of new syringes, these dangers are largely eliminated.

SUMMARY

To overcome these and other disadvantages of the prior art, the present disclosure, briefly described, provides an injection syringe for injecting a fluid into the arterial, venous or muscular system or cavity structures of a patient via subcutaneous, percutaneous, intravascular and other types of injections. The syringe has a hollow syringe body forming a tubular wall, a passageway at a distal end of the tubular wall for passage of fluid into and out of the syringe and a substantially open proximal end for receiving a plunger assembly. The plunger assembly includes a movable plunger disposed within the syringe body. The moveable plunger cooperates with the tubular wall and the distal end of the syringe body to define a fluid chamber of variable volume in fluid communication with the passageway.

Actuating means proximate the open proximal end of the syringe body actuates movement of the plunger. An elastomeric barrier cooperates with the moveable plunger and the open proximal end of the syringe body to define a sterile isolation chamber that effectively seals the actuating means from the interior portions of the syringe, with the barrier in the preferred embodiment being juxtaposed between a first plunger and second plungers, the first plunger acting as a first seal against further migration of bodily fluids toward the actuating means.

The above brief description sets forth rather broadly the more important features of the present invention so that the detailed description of the present invention that follows may be better understood, and so that the present contributions to the art may be better appreciated. There are, of course, additional features of the invention that will be described hereinafter which will form the subject matter of the claims appended hereto.

In this respect, before explaining the several preferred embodiments of the invention in detail, it is to be understood that the invention is not limited in its application to the details of the construction and the arrangements of the components set forth in the following description or illustrated in the drawings. The invention is capable of other embodiments and of being practiced and carried out in various ways. Also, it is to be understood that the phraseology and terminology employed herein are for description and not limitation. Where specific dimensional and material specifications have been included or omitted from the specification or the claims, or both, it is to be understood that the same are not to be incorporated into the appended claims.

As such, those skilled in the art will appreciate that the conception, upon which this disclosure is based, may readily be used as a basis for designing other structures, methods, and systems for carrying out the several purposes of the present invention. It is important, therefore, that the claims are regarded as including such equivalent constructions as far as they do not depart from the spirit and scope of the present invention.

Further, the purpose of the Abstract is to enable the U.S. Patent and Trademark Office and the public generally, and especially the scientists, engineers and practitioners in the art who are not familiar with the patent or legal terms of phraseology, to learn quickly from a cursory inspection the nature and essence of the technical disclosure of the application. Accordingly, the Abstract is intended to define neither the invention nor the application, which is only measured by the claims, nor is it intended to be limiting as to the scope of the invention in any way.

It is therefore an object of the present invention to provide a new and improved injector syringe that provides a reliable and positive barrier against the migration of undesirable fluids therein.

It is another object of the present invention to provide an injector syringe that contains a barrier means that is self-contained, easy to use and relatively inexpensive to manufacture.

It is a further object of the present invention to provide an injector syringe that provides a foolproof barrier means incapably of being defeated by operator error.

An even further object of the present invention to provide an injector syringe that does not require a complicated mechanism to provide an effective barrier against contamination.

Still yet a further object of the present invention to provide an injector syringe that provides a positive barrier means against contamination by blood borne pathogens that do not introduce extraneous materials into a blood stream.

Even yet a further object of the present invention is to provide an injector syringe that prevents contamination of the inner wall of the syringe by substances such as dirt, grease, dust, contrast medium previously used on other patients, blood from other patients, or other substances likely to contact the drive mechanism.

Still another object of the present invention is to provide an injector syringe that can be used multiple times on a single patient, eliminating the possibility of cross-contamination and air emboli injection most acute during the setup procedures used with the installation of new syringes.

These with still other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The disclosure of the improved injector syringe is explained with illustrative embodiments shown in the accompanying drawing, where.

DETAILED DESCRIPTION OF THE PREFERRED EMBODIMENT

Figure 1:
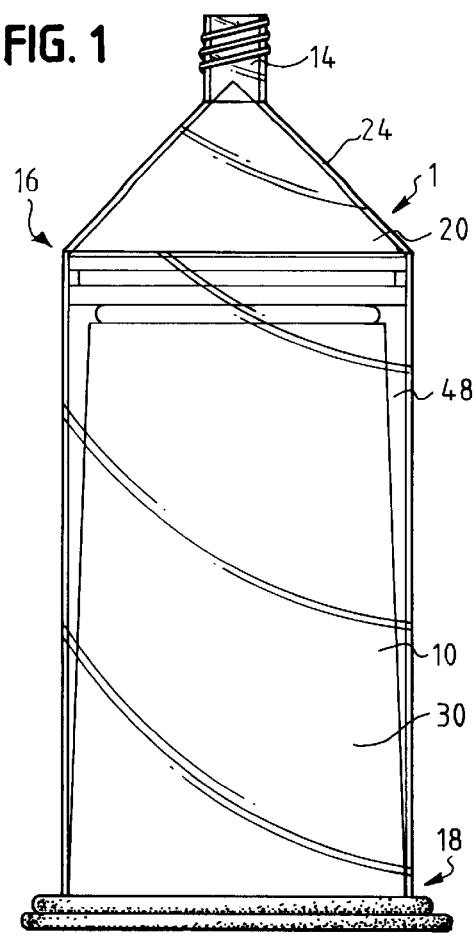
FIG. 1 is an elevation view of a first embodiment of the syringe of the present disclosure, with the first and second plungers in the fully extended position and the barrier means, attached to the plastic second plunger, in a stretched condition.
Figure 2:
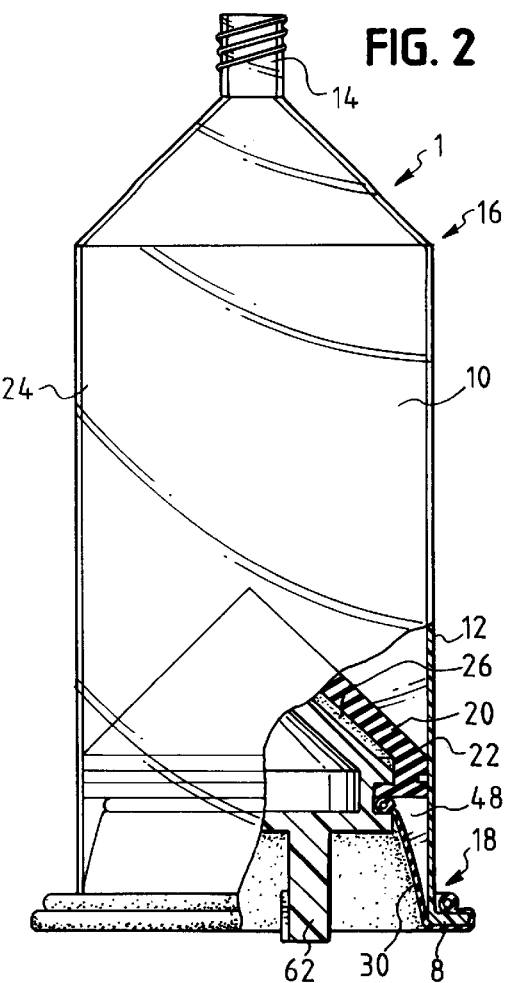
FIG. 2 is an elevation view and partial cross-section view of a first embodiment of the syringe of the present disclosure, with the first and second plungers in the partially retracted position and the barrier means, attached to the plastic second plunger, in a relaxed condition.

Referring now to the drawings, particularly FIGS. 1 and 2, there is shown a first embodiment of the syringe 1 of the present disclosure for injecting a fluid into the arterial, venous, muscular or cavity structures of a patient via subcutaneous, percutaneous, intravascular and other types of injections are widely known and used. The syringe 1 has a hollow syringe body 10 forming a tubular wall 12, a passageway 14 at a distal end 16 of the body 10 for passage of fluid into and out of the syringe 1 and a substantially open proximal end 18 for receiving a plunger assembly. The syringe 1 shown is particularly adapted for use in a power injector syringe in medical applications, but it is understood that the invention may be used with other types of syringes.

Screw threads 4 (shown in FIG. 16) with a linden Luer-lok knurled sleeve 6 enable the attachment of connecting tubing, needles or the like to the tubular distal end 16 of the body 10. The proximal end 18 of the body 10 terminates with an outwardly transversely extending flange 8. A segment of the flange 8 can be removed (not shown) as to known in the art to help alignment of the syringe 1 within a pressure jacket.

A plunger assembly preferably includes a first movable plunger 20 and a second movable plunger 22, each disposed within the tubular wall 12 of the syringe body 10. The first moveable plunger 20, preferably fabricated from an elastomeric material such as rubber, cooperates with the tubular wall 12 and the proximal end 16 of the syringe body 10 to define a fluid chamber 24 of variable volume in fluid communication with the passageway 14. The second plunger 22 cooperates with the first plunger 20 to control movement of the first plunger 20 within the syringe body 10 relative the proximal end 16 of the syringe body 10 to vary the volume of the fluid chamber 24. A chamber 26 is formed between the first plunger 20 and the second plunger 22. In the first and second embodiments, the first rubber plunger 20 and the second plastic plunger 22 are attached one to the other, as further discussed below. In the third and fourth embodiments, movement of the first plunger is obtained by the pressure differentials created by the second plunger (retraction) or by actual force exerted against the first plunger by the second plunger (advancement).

Figure 16:
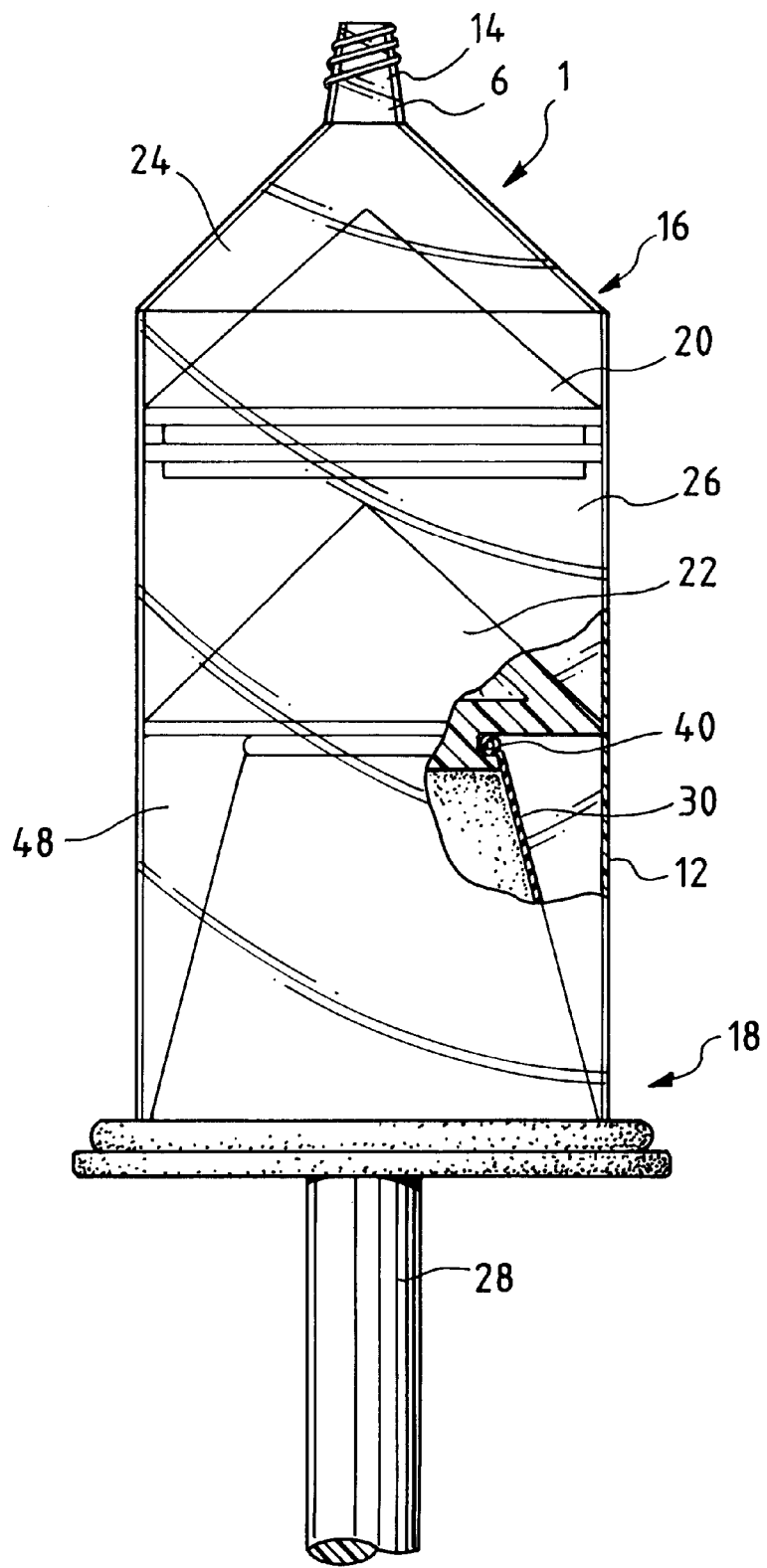
FIG. 16 is an elevation view and partial cross-section view of a fourth embodiment of the syringe of the present disclosure, with the first plunger in the fully extended position, the second plunger in the partially extended position and the barrier means, attached to the second plastic plunger, in a stretched condition.

Actuating means, best shown as injector plunger rod 28 in FIG. 16, is found proximate the open proximal end 18 of the syringe body 10 and directly actuates movement of the second plunger 22, which in turn controls movement of the first plunger 20. As the actuating means 28 retracts the second plastic plunger 22, the first rubber plunger 20 moves with the retracting second plunger 22. The corresponding enlargement of the fluid chamber 24 and the resulting lower pressure therein causes the injected fluid to flow into the syringe body 10 via the passageway 14.

Figure 5:
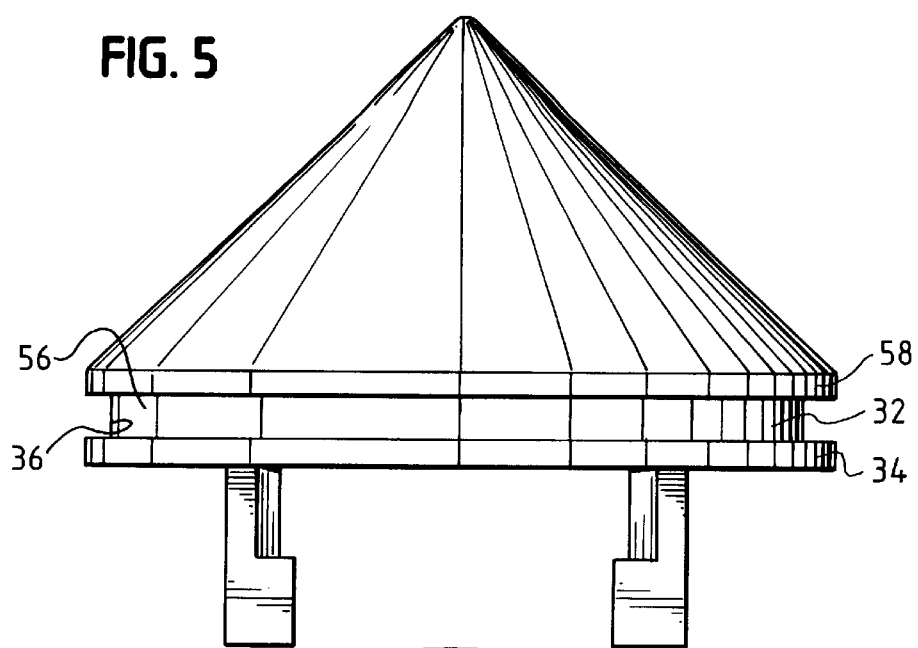
FIG. 5 is an elevation side view of the second plastic plunger of the first embodiment of the syringe of the present disclosure.
Figure 6:
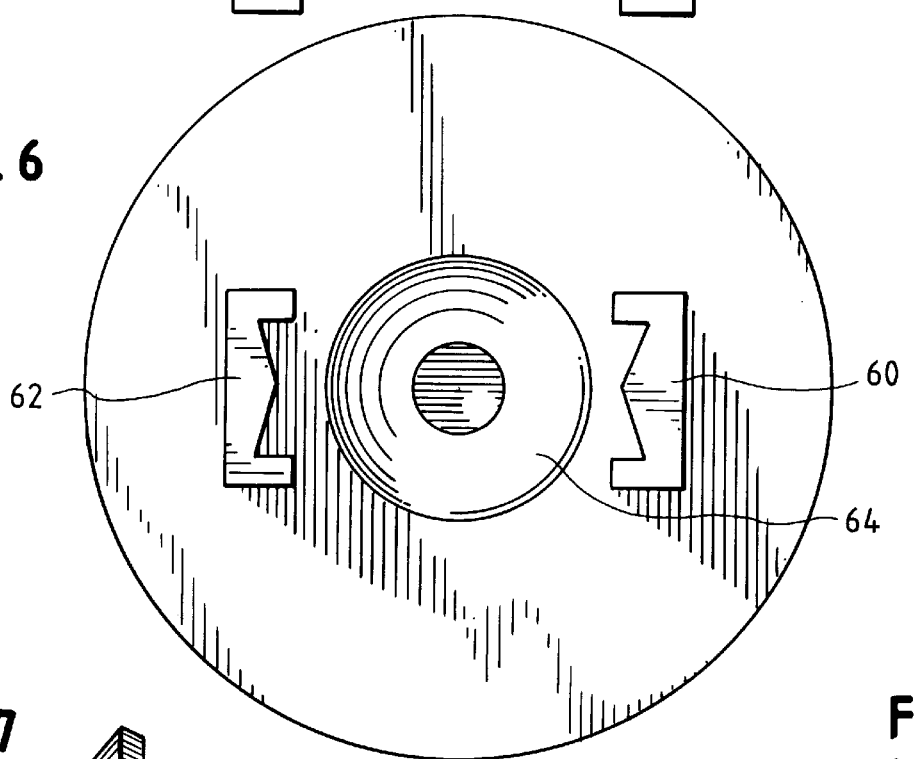
FIG. 6 is a bottom view of the second plastic plunger of FIG. 5 with a view of the winged clasps.
Figure 7:
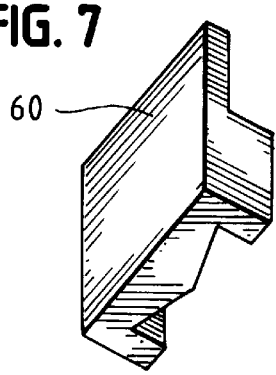
FIG. 7 is a perspective view of the winged clasps of the second plastic head plunger of FIG. 5.
Figure 8:
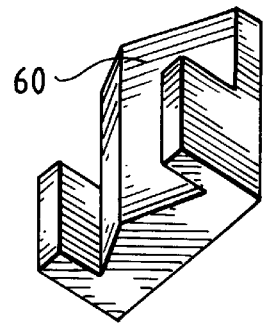
FIG. 8 is second perspective view of the winged clasps of the second head plunger of FIG. 5.
Figure 14:
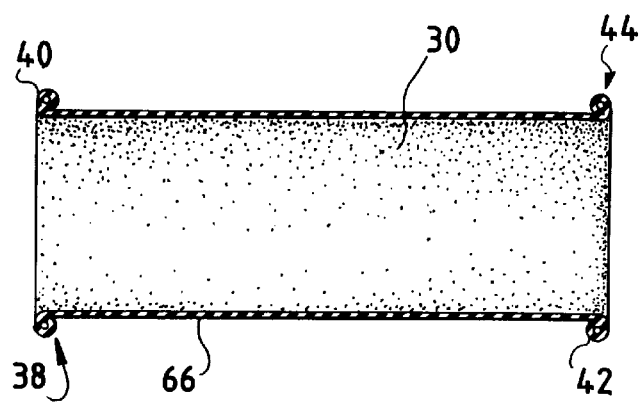
FIG. 14 is a cross-section view of the barrier means of the first, fourth, fifth and sixth embodiments of the syringe of the present disclosure.

A first embodiment of the barrier means 30 of the present invention is shown in FIG. 14, particularly adapted to the first, fourth, fifth and sixth embodiments of the present disclosure, and preferably comprises a thin elastomeric material, such as latex material or like. Other elastomeric materials, such as polyurethane, polypropylene and polyethylene, can be used. Moreover, the barrier means 30 can also take the form of a bellows or other articulated structure that does not rely on its material's elastomeric qualities to provide a seal during motion of the plunger. As better seen in FIG. 5, the barrier means 30 is attached to a base 32 of the second plunger 22.

The second plunger 22 is preferably made from a hard, rigid plastic, with its base 32 including a flange 34 to define an annular channel 36. A first distal end 38 of the first embodiment of the barrier 30, shown in FIG. 14, preferably has a distal elastic ring 40 that encircles and sealingly engages the annular channel 36 of the second plunger 22. A proximal elastic ring 42 at a proximal end 44 of the barrier 30 preferably encircles and sealing engages the flange 8 at the proximal end 18 of the syringe body 10, to which the flange 8 retains the proximal elastic ring 42 in sealing engagement with the syringe body 10. Other means for sealingly attaching the barrier means 30 to the second plunger 22 and/or the proximal end 18 of the syringe body 10 can be used, for example, heat welding and clamping, that might eliminate the need for the rings 40, 42, yet accomplish the sealing objectives of the present invention.

The barrier 30 cooperates with the moveable second plunger 22 and the open proximal end 18 of the syringe body 10 to form a sterile chamber 48 defined by the volume created between the interior of the tubular wall 12, the barrier 30, the proximal end of the syringe body 10, the first rubber plunger 20 and the second plunger 22. The resulting sterile chamber 48 thus effectively seals the actuating means 28 from the interior portions of the syringe 1, especially the fluid chamber 24, with the barrier 30 in the first preferred embodiment being attached to and moving with the second plunger 22. A seal is thereby provided against passage of bodily fluids toward the open proximal end 18 and actuating means 28 and against entry of contaminants via the open proximal end 18 into the syringe body 10.

Figure 9:
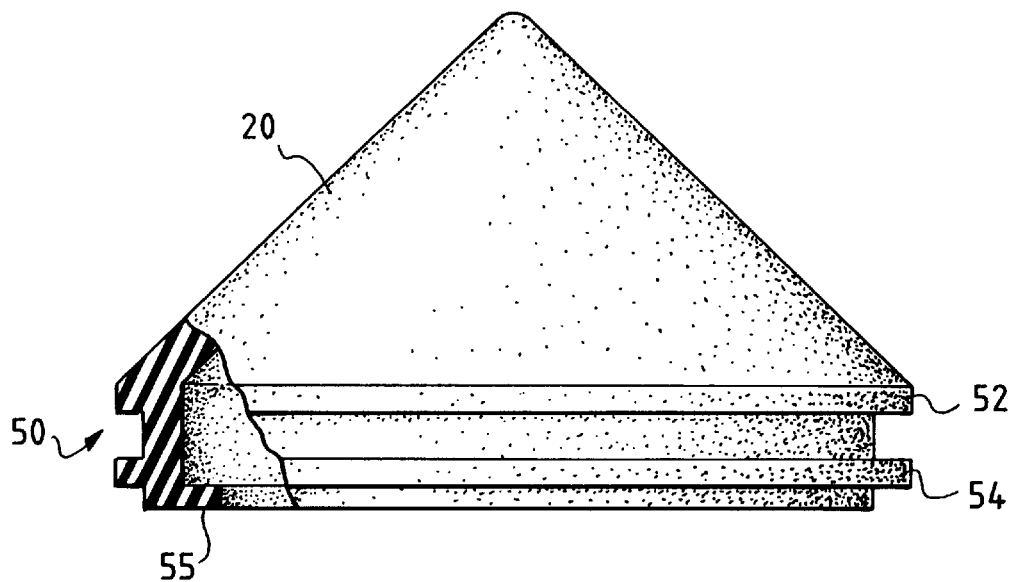
FIG. 9 is an elevation side view of the first rubber plunger of the first embodiment of the syringe of the present disclosure.
Figure 10:
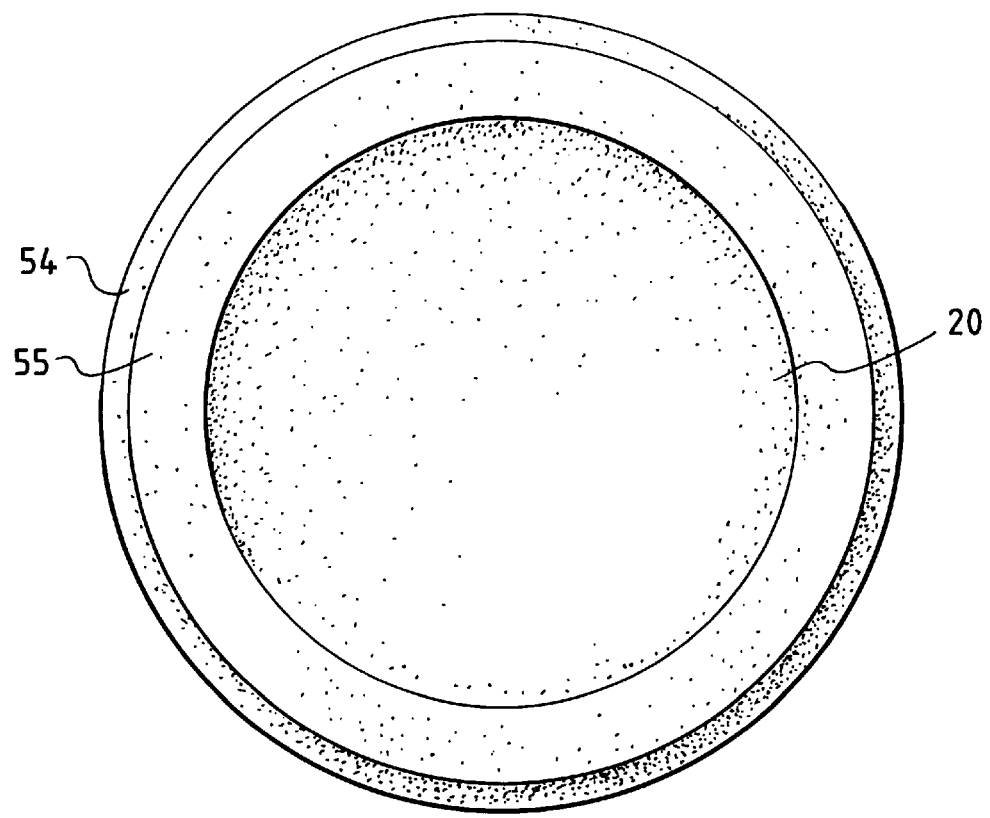
FIG. 10 is a bottom view of the first rubber plunger of FIG. 9.

The first rubber plunger 20 is shown in greater detail in FIGS. 9 and 10. It is preferably of a hollow frustoconical shape better to adapt to the shape of the distal end 16 of the syringe body 10 on its upper side and to the shape of the upper surface of the second plastic plunger 22 on its lower side. The first rubber plunger 20 also is preferably provided at its base 50 with two annular seal members 52, 54 sized sealingly to engage the tubular walls 12 of the inner diameter of the syringe body 10. However, care must be taken in the sizing of the annular seal members 52, 54 so that sealing occurs without binding or excessive friction interfering with the smooth motion of the first rubber plunger 20 within the syringe body 10. The use of two annular seal members 52, 54 spaced apart one from the other also provides an improvement over a single annular seal by reducing tipping or angular displacement of the first rubber plunger 20 within the syringe body 10. An inwardly extending annular lip 55 is also preferably provided to engage the second plastic plunger 22 as discussed below. The annular seal members 52, 54 of the first rubber plunger 20 also prevent spillage or leakage of the contents of the syringe.

Figure 3:
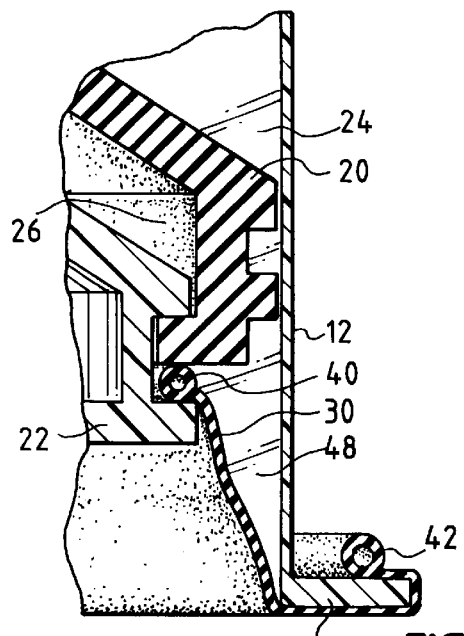
FIG. 3 is an enlarged partial cross-section view of the syringe of FIG. 1, with the first and second plungers in the partially retracted position and the barrier means, attached to the plastic second plunger, in a relaxed condition.

The second plastic plunger 22 is shown in greater detail in FIGS. 5 through 8. It also preferably has a frustoconical shape to adapt to the shape of the lower surface of the first rubber plunger 20 on its upper side. The second plastic plunger 22 is preferably provided at its base 56 with an annular ring member 58 that, with the flange 34, form the annular channel 36. The annular channel 36 is in turn adapted to receive the distal elastic ring 40 of the barrier means 30, as best shown in FIG. 3. Also, the lip 55 of the first rubber plunger 20 is preferably inserted into the annular channel 36 to couple the first rubber plunger 20 and the second plastic plunger 22 one to the other positively and mechanically.

The base 56 of the second plastic plunger 22 is also provided with winged catches 60, 62 or a notched recess 64 that, as is known in the art of injector-type syringes, are adapted to receive the actuating means 28 to engage positively and move the second plastic plunger 22. The winged catches 60, 62 or notch 64 extend from the base or bottom of the second plastic plunger 22 through the open proximal end 18 of the body 10. Preferably, the second plastic plunger 22 is situated within the first rubber plunger 20 and is attached to the first rubber plunger by insertion of the lip 55 into the annular channel 36 of the second plastic plunger 22. The final plunger assembly is thus movable in unison during loading or injection phases.

As the actuating means 28 retracts the second plastic plunger 22, the first rubber plunger 20 follows the retracting movement of the second plastic plunger 22. The corresponding enlargement of the fluid chamber 24 and the resulting lower pressure therein causes the injected fluid to flow into the syringe body 10 via the passageway 14.

Figure 4:
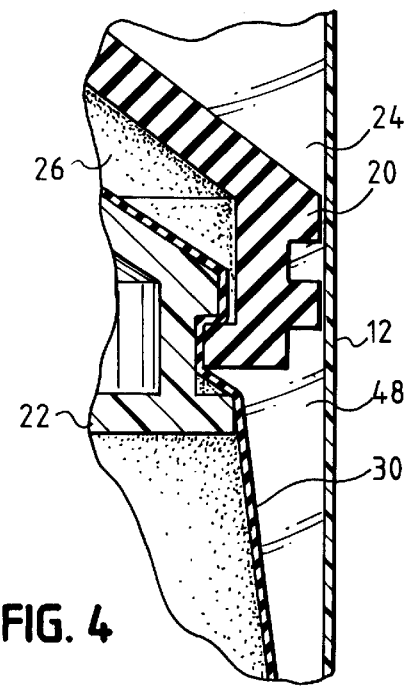
FIG. 4 is an enlarged partial cross-section view of a second embodiment of the syringe of the present disclosure, with the first and second plungers in the extended position and the barrier means, juxtaposed between the first and second plungers, in a stretched condition.
Figure 15:
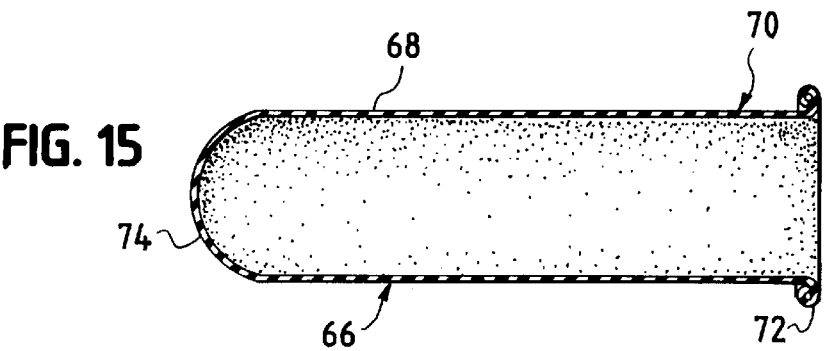
FIG. 15 is a cross-section view of the barrier means of the second and third embodiments of the syringe of the present disclosure.

Another embodiment of the barrier means, applicable to the second and third embodiments of the present disclosure, is shown in FIG. 15, where the barrier means 66 is formed from a closed-ended elastic membrane 68. A proximal end 70 of the barrier means 66 preferably includes an elastic ring 72 that, like the elastic ring 42 of the barrier means 30, attaches to the proximal end 18 of the body 10 about the flange 8 to form a seal thereat. Again, heat welding or clamps may be used to obtain the sealing relationship. The distal end 74 of the barrier means 66 is preferably situated over the second plastic plunger 22 (as shown in FIGS. 4 and 16) and is preferably encased and secured by the first rubber plunger 20 attached to the second plastic plunger 22 (as least as to the second embodiment). With either of the barrier means 30 or 66, advancement of the plunger assembly longitudinally within the body 10 is accomplished with a sterile compartment 48 between the barrier means 30 or 66 and the inside wall 12 of the syringe body 10. When the plunger assembly is retracted, the barrier means 30 or 66 will contract, revealing a sterile inside fluid compartment 24 that can be used multiple times on a single patient.

Figure 13:
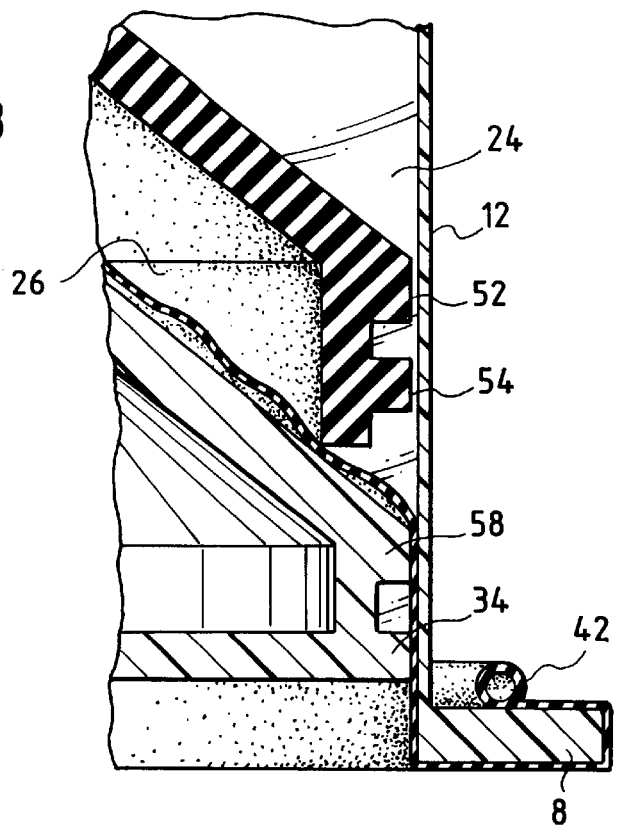
FIG. 13 is an enlarged partial cross-section view of the third embodiment of the syringe of the present disclosure, with the first and second plungers in the partially retracted position and the barrier means, juxtaposed between the first rubber plunger and the second plastic plunger, in a relaxed condition.

In a third and fourth embodiments of the present disclosure, such as shown in FIGS. 13 and 16, respectively, the first rubber plunger 20 and the second plastic plunger 22 are not attached to each other, but rather rely upon the vacuums created during relative movement to cause retraction and literal force against one other to cause advancement within the syringe. In these embodiments, the annular seal member 58 and the annular flange 34 of the second plastic plunger 22 are sized to engage the tubular walls 12 of the inner diameter of the syringe body 10 sealingly, with sufficient clearance for the barrier means 30 or 66. The annular seal member 58 and the flange 34 are preferably sized so that sealing occurs without binding or excessive friction interfering with the smooth motion of the second plastic plunger 22 within the syringe body 10. As with the first rubber plunger 20, the use of the annular seal member 58 and the flange 34, being each spaced apart one from the other to define the annular channel 36, also reduces tipping or angular displacement of the second plastic plunger 22 within the syringe body 10.

As the actuating means 28 retracts the second plastic plunger 22, a pressure vacuum is created in the chamber 26, which in turn causes the first plunger 20 to follow the retracting movement of the second plunger 22. The corresponding enlargement of the fluid chamber 24 and the resulting lower pressure therein causes the injected fluid to flow into the syringe body 10 via the passageway 14. Advancement of both plungers 20, 22 is accomplished by simply the second plunger 22 pushing the first 20 toward the distal end 16 of the syringe 1.

Figure 17:
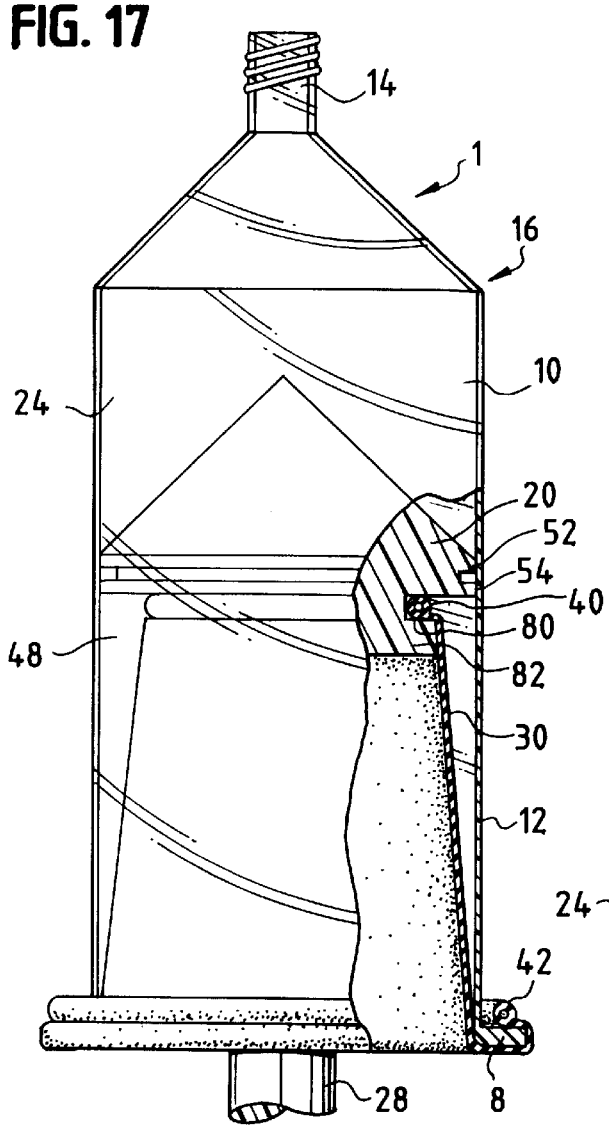
FIG. 17 is an elevation view and partial cross-section view of the syringe of a fifth embodiment of the syringe of the present disclosure, with the barrier means attached to the moveable plunger.
Figure 18:
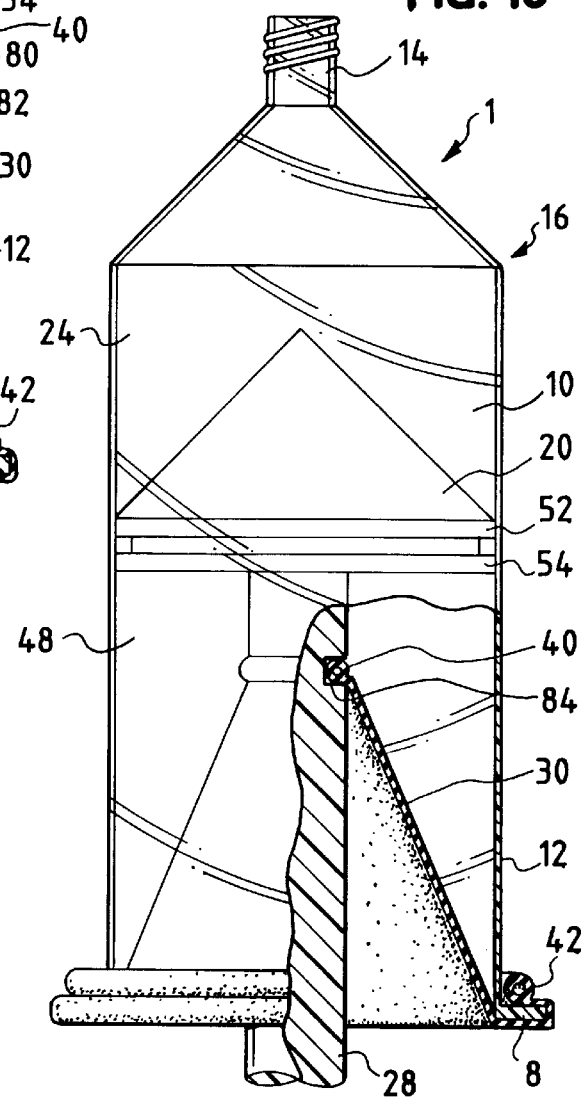
FIG. 18 is an elevation view and partial cross-section view of the syringe of a sixth embodiment of the syringe of the present disclosure, with the barrier means attached to the actuating means.

In the fifth and sixth embodiments of the present disclosure, such as shown in FIGS. 17 and 18, respectively, the barrier 30 is attached to the plunger assembly. In these embodiments, only a single plunger 20, either plastic or rubber, is provided with an annular seal or annular ring member 52, 54. The annular seals 52, 54 are sized to engage the tubular walls 12 of the inner diameter of the syringe body 10 sealingly. The annular seals 52, 54 are preferably sized so that sealing occurs without binding or excessive friction interfering with the smooth motion of the plunger 20 within the syringe body 10. Also, the use of the annular seals 52, 54, being each spaced apart one from the other to define the annular channel 36, also reduces tipping or angular displacement of the plunger 20 within the syringe body 10.

The barrier 30 cooperates with the plunger 20 and the open proximal end 18 of the syringe body 10 to form a sterile chamber 48 defined by the volume created between the interior of the tubular wall 12, the barrier 30, the proximal end of the syringe body 10 and the plunger 20. The resulting sterile chamber 48 thus effectively seals the actuating means 28 from the interior portions of the syringe 1, especially the fluid chamber 24.

The ring 40 of the distal end 38 of the barrier 30 in the fifth embodiment is attached to and moves with the plunger 20 within a channel or notch 80 positioned about a lower portion 82 of the plunger 20. The ring 40 of the distal end 38 of the barrier 30 in the sixth embodiment is attached to a channel or notch 84 in the rod or actuating means 28 and moves with the rod 28. A seal is thereby provided against passage of bodily fluids toward the open proximal end 18 and actuating means 28 and against entry of contaminants via the open proximal end 18 into the syringe body 10.

Before use, the plunger assembly of the syringe 1 is preferably assembled in one of two possible starting positions. In the first position, the plunger assembly is initially positioned within the body 10 against the distal end 16 of the body, with the barrier means 30 or 66 in a fully elongated state. Alteratively, the plunger assembly is initially positioned within the body 10 with the bottom of the base of the second plastic plunger 22 placed proximate the proximal end 18 of the body 10. The barrier means 30 or 66 is in a fully relaxed state.

Figure 12:
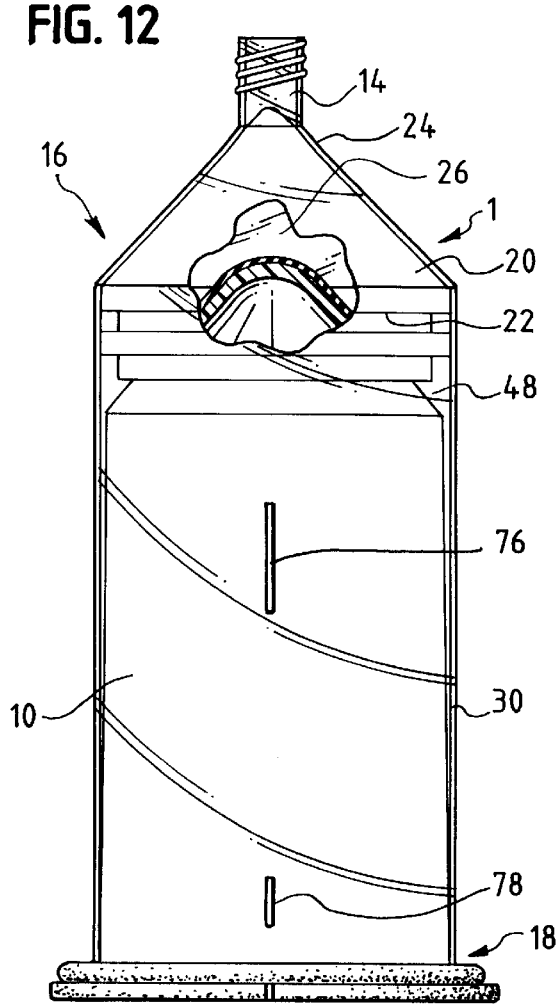
FIG. 12 is an elevation view and partial cross-section view of the syringe of the third embodiment of the syringe of the present disclosure, with the first and second plungers in the fully extended position and the barrier means, juxtaposed between the first rubber plunger and the second plastic plunger, in a stretched condition.
Figure 11:
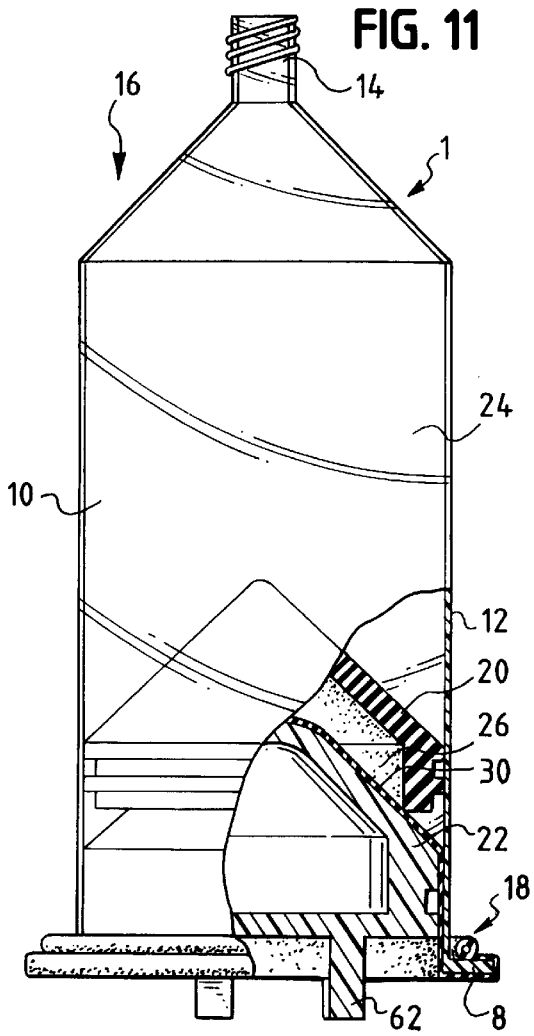
FIG. 11 is an elevation view and partial cross-section view of a third embodiment of the syringe of the present disclosure, with the first and second plungers in the partially retracted position and the barrier means, attached to the plastic second plunger, in a relaxed condition.

In operation, the syringe 1 of the present disclosure is removed from its sterile packaging and mounted into a pressure jacket of a power injection device or affixed to a power injection device by other means. When using a power injector with a pressure jacket position, alignment keys 76 and 78, as shown in FIG. 12, as well as the removed segment of the flange 8, help alignment of the syringe 1 within a pressure jacket. Once the syringe 1 is secured into the pressure jacket, the attachment means holding the installed syringe can be turned so that the winged catches 60, 62 or the notch 64 on the bottom of the second plastic plunger 22 engage the mechanical plunger piston 28 of the power injector. In the fifth and sixth embodiments, the attachment is made directly to the plunger 20.

If the syringe 1 is supplied with the plunger assembly initially positioned proximate the open proximal end 18 of the body 10, the power injector's mechanical plunger piston 28 must be advanced so that the plunger assembly is advanced against the frustoconical shape of the distal end 16 of the body 10. A quick-fill tube, connecting tube, needle or the like may now be attached to the passage 16 of the syringe body 10. Placing the other end of the quick-fill tube, connecting tube, needle or the like into a separate container containing contrast medium or similar substances to be injected, the power injector's mechanical plunger piston 28 is retracted to draw the solution from the container into the chamber 24 of the syringe body 10.

After the desired amount of contrast medium or the like has been drawn into the chamber 24, any entrained air is removed from the syringe to prevent the injection of air emboli into the circulatory system by raising the distal end 16 of the syringe body 10 and slightly advancing the plunger piston 28 and the plunger assembly toward the distal end 16. Quick-fill tubes must be replaced at this point with connecting tubing, needle or the like which is adequate to sustain the pressure generated by the injection to be administered.

If the syringe 1 is supplied with the plunger assembly initially placed proximate the distal end 16 of the syringe body 10, the initial advancement of the power injector's mechanical plunger piston 28 is used to engage the winged catches 60, 62 or notch 64 on the base of the second plastic plunger 22 or plunger 20. The loading procedure is then followed as previously described.

With the syringe in an upright position, the distal end 16 being the highest point, all air is removed from the syringe including the connecting tubing, needle or the like by slowly advancing the mechanical plunger. Once the air is removed, leaving only contrast medium or the like remaining in the chamber 24, the power injector is turned so that the distal end 16 of the syringe 1 is pointing down toward the patient at approximately 135 degrees from the upright position. This is a further safety step so that if bubbles within the syringe 1 are not detected during the filling or connecting sequences, they will float toward the plunger assembly, decreasing the risk of injecting air emboli into the patient.

To inject the contrast medium or the like, the plunger assembly is advanced longitudinally within the body 10, while stretching the barrier means 30 or 66 simultaneously. When the chamber 24 of the syringe 1 is emptied, the filling sequence can be repeated as often as is necessary on the patient. As opposed to the syringes of the prior art, use of the syringe for more than one injection does not result in contamination of the inner wall 12 of the syringe body 10 by substances such as dirt, grease, dust, contrast medium previously used on other patients, blood from other patients, or other substances likely to contact the power injector and the plunger piston 28. This eliminates the risk of cross-contamination of certain diseases from patient to patient such as Hepatitis B, Hepatitis C, Aids and other blood-borne pathogens. The syringe of the present disclosure, provided with the barrier means 30 or 66, is designed to isolate the sterile inner wall 12 and fluid chamber 24 of the syringe body 10 from contaminating particles that may fall from the power injector or the plunger piston 28 into the open proximal end 18 of the syringe body 10. Likewise, blood-borne contaminants that pass past the first plunger from the fluid chamber 24 are contained within the isolation chamber 48 and are unable to contaminate the drive mechanism and also offers protection for the operator of the equipment.

The barrier means 20 or 66, or membrane, however, does not contact the contrast medium or the like eliminating reactions due to latex sensitive patients in those cases where latex is used or generally the contamination that is invariably present in other types of materials. Thus, the syringe 1 of the present invention can be used multiple times on a single patient, thereby greatly reducing the possibility of cross-contamination and air emboli injection typically associated with the use of multiple syringes for a single patient during a single injection session.

Both the syringe body 10 and the plungers 20, 22 can be formed from molded plastic. In the first four embodiments, the first rubber plunger 20 is preferably formed from rubber or similar elastomeric material. The barrier means 30 or 66 is preferably formed from an elastic material, such as certain rubbers, plastics, latex or the like which are suitable for use. Preferably the components of the syringe 1 of the present disclosure cannot be separated for cleaning or reuse, it being contemplated that the syringe 1 of the present disclosure is adapted for use with only a single patient.

It is also contemplated that the syringe assembly herein revealed can be used for hand injections, particularly those ranging from 1 to 60 cc of fluid. There, the plunger arm 28 is permanently affixed to the plunger 20 or second plastic plunger 22. Syringes with capacities exceeding 60 cc are normally used by power injectors.

The advantages of the improved syringe are attained in an economical, practical and facile manner. To wit, an effective new syringe has been developed.

While embodiments of the improved injector syringe have been herein illustrated and described, it is to be appreciated that various changes, rearrangements and modifications may be made therein, without departing from the scope of the invention as defined by the appended claims.

What is claimed:

1. An injection syringe for injecting a fluid into a patient comprising;
   a hollow syringe body having a tubular wall, a passageway at a distal end thereof for passage of said fluid into and out of said syringe and an open proximal end for receiving a plunger assembly;
   said plunger assembly comprising a movable plunger disposed within said syringe body, said moveable plunger having an annular seal disposed between a distal end and a proximal end thereof, wherein said distal end and said annular seal of said moveable plunger cooperate with said tubular wall and said distal end of said syringe body to define a fluid chamber of variable volume in fluid communication with said passageway, said annular seal isolating said proximal end of said moveable plunger from said fluid chamber;
   said plunger assembly further comprising actuating means disposed proximate said open proximal end of said syringe body attached to said proximal end of said moveable plunger for actuating movement of said moveable plunger; and
   barrier means having a distal end and a proximal end, said distal end sealingly attached to said plunger assembly and said proximal end sealingly attached to said open proximal end of said syringe body, said barrier means extending between said annular seal and said open proximal end of said syringe body for sealing said fluid in said fluid chamber from said actuating means, said annular seal further isolating said barrier means from said fluid chamber.

2. The injection syringe of claim 1 where said actuating means is cooperatively attachable to said plunger.

3. The injection syringe of claim 1 wherein said barrier means is an elastomeric membrane occluding the diameter of said hollow syringe body and located between said annular seal and said proximal end of said syringe body.

4. The injection syringe of claim 3 wherein said proximal end of said elastomeric membrane further comprises an elastomeric ring in sealing relationship with and around said open proximal end of said hollow syringe body.

5. The injection syringe of claim 3 wherein said distal end of said elastomeric membrane further comprises an elastomeric ring in sealing relationship with and around said proximal end of said moveable plunger.

6. The injection syringe of claim 4 wherein an annular channel is disposed around said proximal end of said moveable plunger for receiving said distal end of said elastomeric membrane.

7. The injection syringe of claim 6 wherein said moveable plunger comprises an upper portion in fluid contact with said fluid chamber and a lower portion in fluid isolation from said fluid chamber, said lower portion comprising a base portion having an outwardly facing annular lip disposed below said annular seal to define said annular channel.

8. The injection syringe of claim 3 wherein said distal end of said elastomeric membrane further comprises an elastomeric ring in sealing relationship with and around said actuating means.

9. The injection syringe of claim 8 wherein said actuating means comprises a rod having an annular channel for receiving said distal end of said elastomeric membrane.

10. The injection syringe of claim 1 wherein said barrier means comprises a bellows occluding the diameter of said hollow syringe body.

11. The injection syringe of claim 1 wherein said distal end of said barrier means is attached to said plunger assembly by heat welding.

12. The injection syringe of claim 1 wherein said proximal end of said barrier means is attached to said proximal end of said syringe body by heat welding.

13. The injection syringe of claim 1 wherein said distal end of said barrier means is clamped to said plunger assembly.

14. The injection syringe of claim 1 wherein said proximal end of said barrier means is clamped to said proximal end of said syringe body.

15. An injection syringe for injecting a fluid into a patient comprising;
   a hollow syringe body having a tubular wall, a passageway at a distal end thereof for passage of said fluid into and out of said syringe and an open proximal end for receiving a plunger assembly;
   said plunger assembly further comprising a movable plunger disposed within said syringe body, said moveable plunger having an annular seal disposed between a distal end and a proximal end thereof, wherein said distal end and said annular seal of said moveable plunger cooperate with said tubular wall and said distal end of said syringe body to define a fluid chamber of variable volume in fluid communication with said passageway, said annular seal isolating said proximal end of said moveable plunger from said fluid chamber;
   means disposed proximate said open proximal end of said syringe body attached to said proximal end of said moveable plunger for actuating movement of said moveable plunger; and
   barrier means sealingly extending from said proximal end of said moveable plunger to said open proximal end of said syringe body for sealing said fluid in said fluid chamber from said actuating means, said barrier means being disposed between said annular seal and said proximal end of the syringe body whereby said annular seal further isolates said barrier means from said fluid chamber.

16. The injection syringe of claim 15 where said actuating means is cooperatively attachable to said plunger.

17. The injection syringe of claim 15 wherein said barrier means is an elastomeric membrane occluding the diameter of said hollow syringe body.

18. The injection syringe of claim 17 wherein said proximal end of said elastomeric membrane further comprises an elastomeric ring in sealing relationship with and around said open proximal end of said hollow syringe body.

19. The injection syringe of claim 17 where said distal end of said elastomeric membrane further comprises an elastomeric ring in sealing relationship with and around said proximal end of said moveable plunger.

20. The injection syringe of claim 19 wherein an annular channel is disposed around said proximal end of said moveable plunger for receiving said distal end of said elastomeric membrane.

21. The injection syringe of claim 20 wherein said moveable plunger comprises an upper portion in fluid contact with said fluid chamber and a lower portion in fluid isolation from said fluid chamber, said lower portion comprising a base portion having an outwardly facing annular lip disposed below said annular seal to define said annular channel.

22. An injection syringe for injecting a fluid into a patient comprising;
    a hollow syringe body having a tubular wall, a passageway at a distal end thereof for passage of said fluid into and out of said syringe and an open proximal end for receiving a plunger assembly;
    said plunger assembly further comprising a movable plunger disposed within said syringe body, said moveable plunger having an annular seal disposed between a distal end and a proximal end thereof, wherein said distal end and said annular seal of said moveable plunger cooperate with said tubular wall and said distal end of said syringe body to define a fluid chamber of variable volume in fluid communication with said passageway, said annular seal isolating said proximal end of said moveable plunger from said fluid chamber;
    means disposed proximate said open proximal end of said syringe body attached to said proximal end of said moveable plunger for actuating movement of said moveable plunger; and
    barrier means sealingly extending from said actuating means to said open proximal end of said syringe body for sealing said fluid in said fluid chamber from said actuating means, said barrier means being disposed between said annular seal and said proximal end of the syringe body whereby said annular seal further isolates said barrier means from said fluid chamber.

23. The injection syringe of claim 22 where said actuating means is cooperatively attachable to said plunger.

24. The injection syringe of claim 22 wherein said barrier means is an elastomeric membrane occluding the diameter of said hollow syringe body.

25. The injection syringe of claim 24 wherein said proximal end of said elastomeric membrane further comprises an elastomeric ring in sealing relationship with and around said open proximal end of said hollow syringe body.

26. The injection syringe of claim 25 wherein said distal end of said elastomeric membrane further comprises an elastomeric ring in sealing relationship with and around said actuating means.

27. The injection syringe of claim 26 wherein said actuating means comprises a rod having an annular channel for receiving said distal end of said elastomeric membrane.

28. An injection syringe for injecting a fluid into a patient comprising;
    a hollow syringe body having a tubular wall, a passageway at a distal end thereof for passage of said fluid into and out of said syringe and an open proximal end for receiving a plunger assembly;
    said plunger assembly further comprising a first movable plunger and a second movable plunger, each disposed within said syringe body, wherein said first moveable plunger cooperates with said tubular wall and said distal end of said syringe body to define a fluid chamber of variable volume in fluid communication with said passageway and said second plunger cooperates with said first plunger to control movement of said first plunger within said syringe body relative said proximal end of the syringe body to vary the volume of said fluid chamber;
    means disposed proximate said open proximal end of said syringe body for actuating movement of said second plunger; and
    barrier means sealingly extending from said moveable second plunger to said open proximal end of said syringe body for sealing said fluid in said fluid chamber from said actuating means.

29. The injection syringe of claim 28 where said actuating means is cooperatively attachable to said second plunger.

30. The injection syringe of claim 28 wherein said barrier means is an elastomeric membrane occluding the diameter of said hollow syringe body.

31. The injection syringe of claim 30 wherein said elastomeric membrane has a distal and a proximal end, said proximal end further comprising an elastomeric ring in sealing relationship with and around said open proximal end of said hollow syringe body.

32. The injection syringe of claim 31, wherein said distal end of the elastomeric membrane is juxtaposed between said first and said second plungers.

33. The injection syringe of claim 28 wherein said distal end further comprises an elastomeric ring in sealing relation to and around a base portion of said second plunger, whereby said elastomeric ring is attached to said second plunger.

34. The injection syringe of claim 28 wherein said barrier means has a distal end and a proximal end, said proximal end of the barrier means comprising a first elastomeric ring in sealing relationship with and around said open proximal end of said syringe body and said distal end of said barrier means comprising a second elastomeric ring in sealing relationship with and around a base portion of said second plunger.

35. The injection syringe of claim 34 wherein said base portion of the second plunger further comprises an annular channel within which said second elastomeric ring is received.

36. The injection syringe of claim 35 wherein said first plunger comprises an upper surface and a lower surface defining a substantially hollow cavity into which said second plunger extends, said first plunger further comprising a base portion having an inwardly facing annular lip extending into said hollow cavity and into said annular channel of said second plunger.

37. The injection syringe of claim 28 wherein said barrier means has a distal end and a proximal end, said proximal end of the barrier means further comprising an elastomeric ring in sealing relation to and around said open proximal end of said syringe body and said distal end of said barrier means further comprising a closed-end membrane juxtaposed between said first and second plunger.

38. The injection syringe of claim 28 wherein said first plunger is moved within said syringe body by pressure differentials created by the motion of said second plunger within said syringe body.

39. An injection syringe comprising:

movable plunger means disposed within the syringe for admitting fluid into said syringe and for forcing fluid from said syringe into the vascular system of a patient, said syringe and said plunger means defining a sterile fluid chamber in communication with a passageway for entry of said fluid into and exit of said fluid out of said sterile fluid chamber;

drive means disposed proximate an open end of said syringe and in cooperative relationship with said plunger means for retracting said plunger means in said syringe to admit fluid into said sterile fluid chamber and for advancing said plunger means in said syringe to force the fluid from said sterile fluid chamber in the injection operation; and barrier means in sealing relationship with each of said plunger means and said open end of said syringe defining an isolation chamber between said sterile fluid chamber and said open end of said syringe for preventing passage of fluid from said sterile fluid chamber to said open end of said syringe and for preventing passage of matter into the fluid chamber from said open end of said syringe, said barrier means being further isolated from contact with said sterile fluid chamber by said plunger means.

40. The syringe of claim 39 wherein said syringe has a passageway at a distal end thereof and said moveable plunger means comprises a first movable plunger and a second movable plunger, each disposed within said syringe, wherein said first moveable plunger cooperates with said tubular wall and a proximal end of said syringe to define a fluid chamber of variable volume in fluid communication with said passageway and said second plunger cooperates with said first plunger to control movement of said first plunger within said syringe relative said distal end of the syringe to vary the volume of said fluid chamber.

41. The syringe of claim 39 wherein said syringe has an open proximal end and said barrier means comprises an elastomeric membrane having a distal and a proximal end, said proximal end further comprising an elastomeric ring in sealing relationship with and around said open proximal end of said syringe and occluding said syringe between said drive means and said distal end.

42. The syringe of claim 39 wherein said syringe has an open proximal end and said barrier means comprises an elastomeric membrane having a distal and a proximal end, said proximal end comprising an elastomeric ring in sealing relationship with and around said open proximal end of said syringe and said distal end of said barrier means comprising a second elastomeric ring in sealing relationship with and around a base portion of said second plunger.

43. The syringe of claim 40 wherein said syringe has an open proximal end and said barrier means comprises an elastomeric membrane having a distal and a proximal end, said proximal end comprising an elastomeric ring in sealing relationship with and around said open proximal end of said syringe and said distal end of said barrier means comprising a closed-end membrane juxtaposed between said first and second plunger.

44. The syringe of claim 39 wherein said barrier means extends between an interior structure and an exterior structure.

45. An injection syringe for automatically injecting a fluid into a patient comprising;

a hollow syringe body having a tubular wall, a passageway at a distal end thereof for passage of said fluid into and out of said syringe and an open proximal end for receiving a plunger assembly;

said plunger assembly further comprising a first movable plunger and a second movable plunger, each disposed within said syringe body, wherein said first moveable plunger cooperates with said tubular wall and said distal end of said syringe body to define a fluid chamber of variable volume in fluid communication with said passageway and said second plunger cooperates with said first plunger to control movement of said first plunger within said syringe body relative said proximal end of the syringe body to vary the volume of said fluid chamber;

control means disposed proximate said open proximal end of said syringe body for actuating movement of said second plunger; and barrier means sealingly extending from said moveable second plunger to said open proximal end of said syringe body for sealing said fluid in said fluid chamber from said actuating means.

46. The injection syringe of claim 45 further comprising mounting means for supporting at least one syringe for an injection operation, and comprising actuating means adjacent said plunger means for controlling the movement of said plunger in said syringe.

47. The injection syringe of claim 45 wherein second plunger further comprises a base portion having therein an annular channel and said barrier means has a distal end and a proximal end, said proximal end of the barrier means comprising a first elastomeric ring in sealing relationship with and around said open proximal end of said syringe body and said distal end of said barrier means comprising a second elastomeric ring in sealing relationship within and around an annular channel of said second plunger.

48. The injection syringe of claim 45 wherein said first plunger further comprises an upper surface and a lower surface defining a substantially hollow cavity into which said second plunger extends, said first plunger further comprising a base portion having an inwardly facing annular lip extending into said hollow cavity and into an annular channel of said second plunger.

49. The injection syringe of claim 45 wherein said barrier means has a distal end and a proximal end, said proximal end of the barrier means further comprising an elastomeric ring in sealing relationship with and around said open proximal end of said syringe body and said distal end of said barrier means further comprising a closed-end membrane juxtaposed between said first and second plunger.

50. An injection syringe for injecting a fluid into a patient comprising;

a hollow syringe body having a tubular wall, a passageway at a distal end thereof for passage of said fluid into and out of said syringe and an open proximal end for receiving a plunger assembly;

said plunger assembly comprising a movable plunger disposed within said syringe body, said moveable plunger having an annular seal disposed between a distal end and a proximal end thereof, wherein said distal end and said annular seal of said moveable plunger cooperate with said tubular wall and said distal end of said syringe body to define a fluid chamber of variable volume in fluid communication with said passageway, said annular seal isolating said proximal end of said moveable plunger from said fluid chamber;

actuating means disposed proximate said open proximal end of said syringe body attached to said proximal end of said moveable plunger for actuating movement of said moveable plunger; and barrier means having a distal end and a proximal end, said distal end sealingly attached to said plunger assembly and said proximal end sealingly attached to said open proximal end of said syringe body to define an isolation chamber isolating said fluid chamber from said proximal end of said syringe body, said barrier means being further isolated from contact with said sterile fluid chamber by said annular seal of said moveable plunger.

* * * * *

UNITED STATES PATENT AND TRADEMARK OFFICE
CERTIFICATE OF CORRECTION

PATENT NO.   : 5,976,112
DATED        : November 2, 1999
INVENTOR(S)  : Henry W. Lyza, Jr.

It is certified that error appears in the above-identified patent and that said Letters Patent is hereby corrected as shown below:

On the title page: Item [73] Assignee: should read

"LyZa" should be -- Lyza --;

Column 1, line 19;
    "use" should be -- used --;

Column 1, lines 54 and 55;
    Delete "autoimmunity deficiency" and substitute -- immunodeficiency --;

Column 4, line 42;
    Before "to provide" insert -- is --;

Column 4, line 46;
    Before "to provide" insert - is --;

Column 6, line 36;
    Before "known" delete "to";

Column 7, line 20;
    "sealing" should be -- sealingly --;

UNITED STATES PATENT AND TRADEMARK OFFICE
CERTIFICATE OF CORRECTION

PATENT NO. : 5,976,112
DATED : November 2, 1999
INVENTOR(S) : Henry W. Lyza, Jr.

It is certified that error appears in the above-identified patent and that said Letters Patent is hereby corrected as shown below:

Column 8, line 50;
        Before "third and fourth" delete "a" and substitute -- the --;

Column 10, line 57;
        "Aids" should be -- AIDS --;

Column 11, line 66;
        "where" should be -- wherein --;

Column 13, line 6;
        "where" should be -- wherein --;

Signed and Sealed this

Seventh Day of November, 2000

Attest:

Q. TODD DICKINSON

*Attesting Officer*      *Director of Patents and Trademarks*